United States Patent [19]

Merry

[11] 4,275,728

[45] Jun. 30, 1981

[54] ANESTHESIA DEVICE

[75] Inventor: Jack D. Merry, Summerville, S.C.

[73] Assignee: The Kendall Company, Boston, Mass.

[21] Appl. No.: 124,188

[22] Filed: Feb. 25, 1980

[51] Int. Cl.³ .............................................. A61M 5/00
[52] U.S. Cl. .................................................... 128/215
[58] Field of Search ............ 128/215, 216, 221, 214.4, 128/218 R, 347, 348

[56] References Cited

U.S. PATENT DOCUMENTS

| | | | |
|---|---|---|---|
| 2,700,385 | 1/1955 | Ortiz | 128/215 |
| 2,712,314 | 7/1955 | Kohl | 128/215 |
| 2,740,404 | 4/1956 | Kohl | 128/215 |
| 3,995,629 | 12/1976 | Patel | 128/215 |

*Primary Examiner*—John D. Yasko
*Attorney, Agent, or Firm*—Powell L. Sprunger

[57] ABSTRACT

A device for performing an anesthesia procedure on a patient comprising, a needle assembly having an elongated hollow needle with a distal tip, and a connecting member attached to a proximal end of the needle, with the connecting member having an elongated distally directed control member generally aligned with and spaced from the needle. The device has a sleeve assembly having an elongated hollow sleeve to slidably receive the needle, and an abutment member attached to a proximal end of the sleeve. The abutment member has a first proximal stop member to abut against a distal portion of the control member in a configuration of the needle assembly at a first rotational position with the needle tip retracted within the sleeve assembly, and a guide device to releasably retain the needle assembly at the first rotational position. The abutment member has a second intermediate stop member to abut against the distal portion of the control member in a configuration of the needle assembly at a second rotational position with the needle tip extending an intermediate distance from the sleeve assembly, and a guide device to releasably retain the needle assembly at the second rotational position. The abutment member has a third distal stop member to abut against the distal portion of the control member in a configuration of the needle assembly at a third rotational position with the needle tip extending a maximum distance from the sleeve assembly, and a guide device to releasably retain the needle assembly at the third rotational position.

8 Claims, 13 Drawing Figures

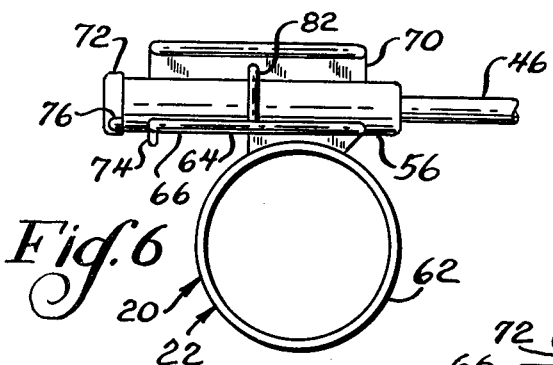
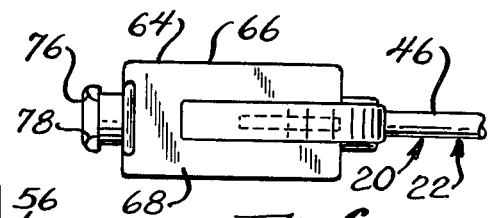
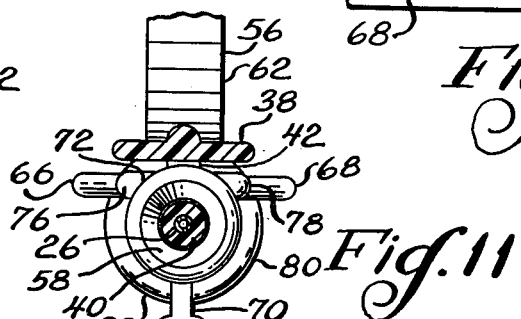
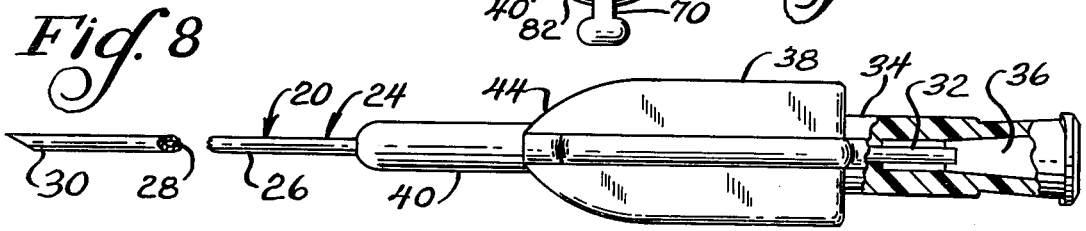
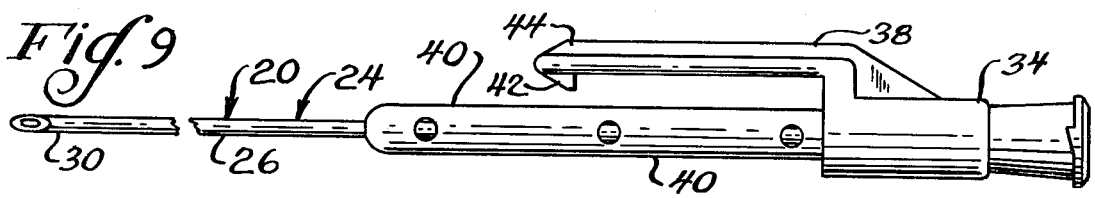
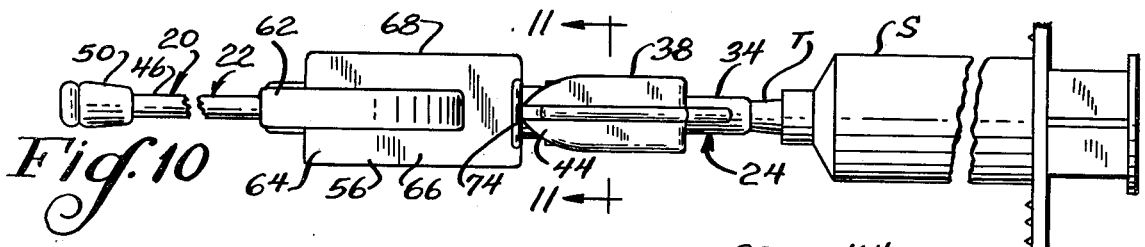
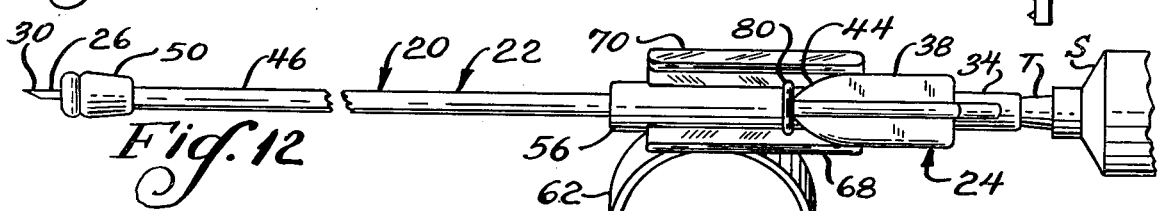
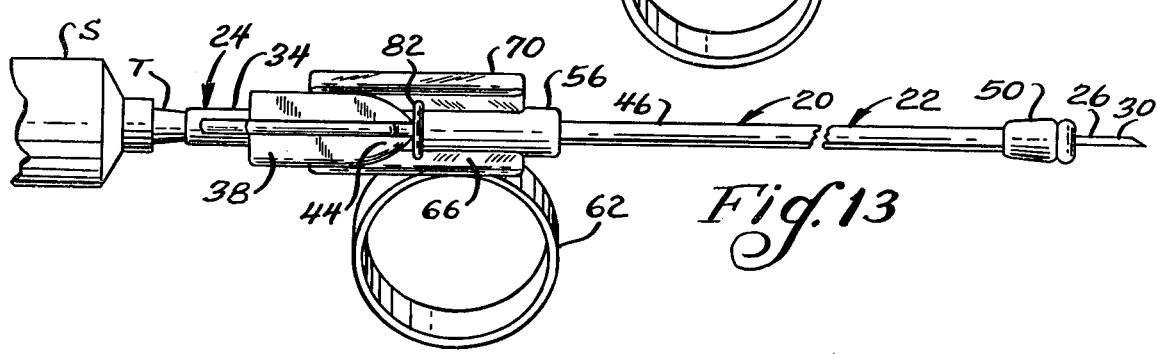

ANESTHESIA DEVICE

BACKGROUND OF THE INVENTION

The present invention relates to devices for performing an anesthesia procedure.

During childbirth, paracervical and transpudendal anesthesia procedures are commonly used to reduce pain during the first and second stages of labor. The first stage of labor may be defined as the period of time between the onset of labor and the time at which the cervix has completely dilated. The second stage of labor takes place between the time at which the cervix has completely dilated and the time of child delivery. Pain during the first stage of labor is primarily caused by effacement and dilation of the cervix, and may be relieved by a paracervical block. Pain during the second stage of labor results from dilation of the vagina, pressure exerted against the pelvic bones, and episiotomy, and may be relieved with a pudendal block.

The paracervical anesthesia procedure is normally performed when the cervix has dilated approximately 4 centimeters, with uterine contractions taking place at approximately 5 minute intervals and lasting at least 30 seconds. The paracervical block may be either a single injection or a continuous type, and is performed to block the nerves around the cervical opening.

During the procedure, the physician inserts a needle and catheter assembly into the vagina with the needle retracted within the assembly, and places the distal end of the assembly against the ligament at the vaginal fornix immediately lateral to its junction with the cervix. Next, the needle is pushed out of the assembly by the physician, and should penetrate the mucosa approximately 1.0 to 1.5 centimeters, after which the anesthetic solution is injected through the needle into the mucosa. In this manner, the anesthetic solution may be injected at 3 or 4 and 8 or 9 o'clock positions into the mucosa around the cervix to obtain the paracervical block.

When the cervix has almost fully dilated, the transpudendal anesthesia procedure is performed to relieve pain during the second stage of labor. In this procedure, the anesthetic solution is injected into the wall of the vagina.

SUMMARY OF THE INVENTION

The principal feature of the present invention is the provision of an improved device for performing an anesthesia procedure.

The anesthesia device comprises, a needle assembly having an elongated hollow needle with a distal tip, and a connecting member attached to a proximal end of the needle, with the connecting member having an elongated distally directed control member generally aligned with and spaced from the needle. The device has a sleeve assembly having an elongated hollow sleeve to slidably receive the needle, and an abutment member attached to a proximal end of the sleeve. The abutment member has a first proximal stop member to abut against a distal portion of the control member in a configuration of the needle assembly at a first rotational position with the needle tip retracted within the sleeve assembly, and guide means to releasably retain the needle assembly at the first rotational position. The abutment member has a second intermediate stop member to abut against the distal portion of the control member in a configuration of the needle assembly at a second rotational position with the needle tip extending an intermediate distance from the sleeve assembly, and guide means to releaseably retain the needle assembly at the second rotational position. The abutment member has a third distal stop member to abut against the distal portion of the control member in a configuration of the needle assembly at a third rotational position with the needle tip extending a maximum distance from the sleeve assembly, and guide means to releasably retain the needle assembly at the third rotational position.

A feature of the present invention is that the device may be readily positioned in the patient with the needle assembly at the first rotational position and with the needle tip retracted within the sleeve assembly.

Another feature of the invention is that when the device has been placed in the patient, the needle assembly may be readily rotated to the second or third position to cause insertion of the needle tip into the patient's body a selected distance.

Yet another feature of the invention is that the device may be manipulated in a simplified manner.

Further features will become more fully apparent in the following description of the embodiments of this invention and from the appended claims.

DESCRIPTION OF THE DRAWINGS

In the drawings:

FIG. 6 is a fragmentary elevational view of the other side of the sleeve assembly for the device of FIG. 1;

FIG. 7 is a fragmentary lower plan view of the sleeve assembly of FIG. 2;

FIG. 8 is a fragmentary upper plan view, partly broken away, of a needle assembly for the device of FIG. 1;

FIG. 9 is a fragmentary elevational view of the needle assembly of FIG. 8;

FIG. 10 is a fragmentary lower plan view of the anesthesia device showing the needle assembly at a first rotational position relative to the sleeve assembly;

FIG. 11 is a sectional view taken substantially as indicated along the line 11—11 of FIG. 10;

FIG. 12 is a fragmentary perspective view of the anesthesia device showing the needle assembly at a second rotational position relative to the sleeve assembly; and FIG. 13 is a fragmentary perspective view of the anesthesia device showing the needle assembly at a third rotational position relative to the sleeve assembly.

DESCRIPTION OF THE PREFERRED EMBODIMENTS

Figure 1:
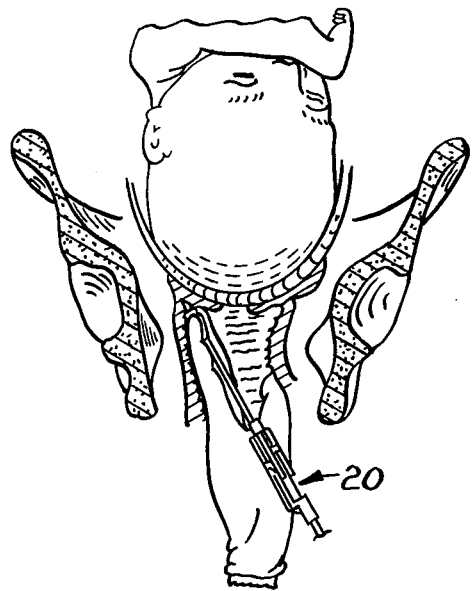
FIG. 1 is a fragmentary perspective view of the device of the present invention as positioned for performing a paracervical anesthesia procedure.
Figure 2:
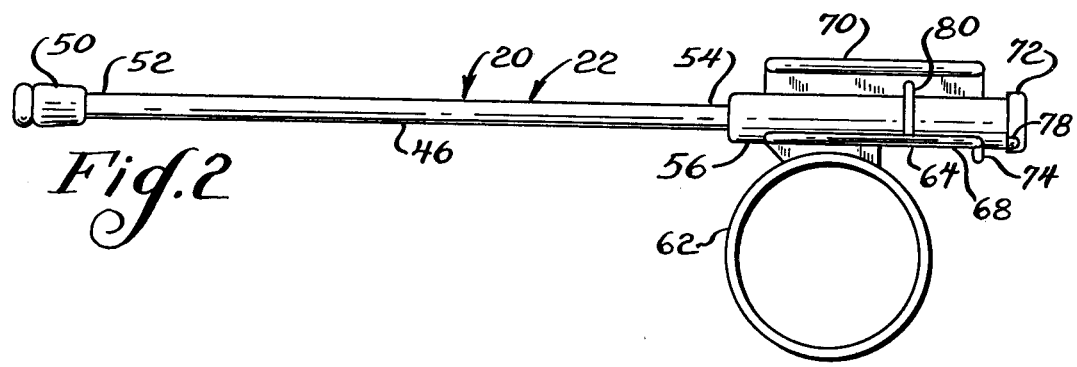
FIG. 2 is an elevational view of a sleeve assembly for the device of FIG. 1.
Figure 3:
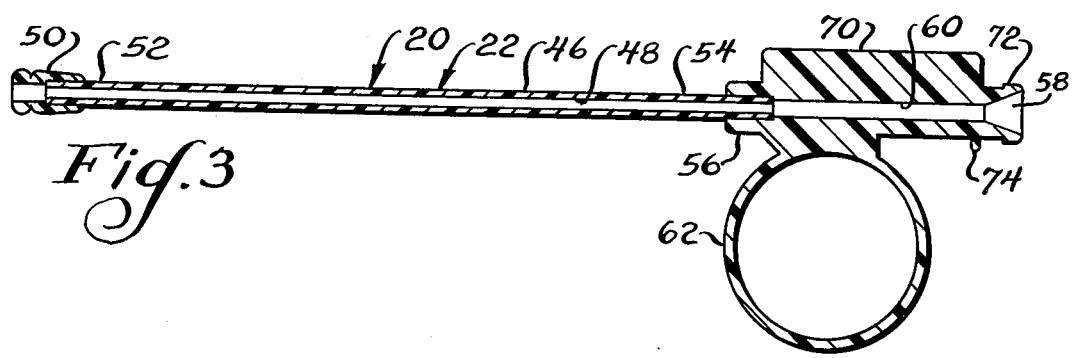
FIG. 3 is a sectional view of the sleeve assembly of FIG. 2.
Figure 4:
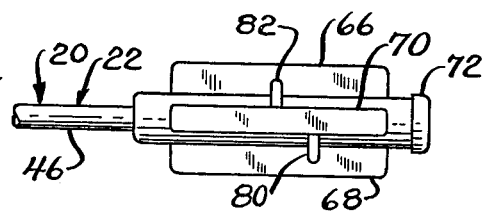
FIG. 4 is a fragmentary top plan view of the sleeve assembly of FIG. 2.
Figure 5:
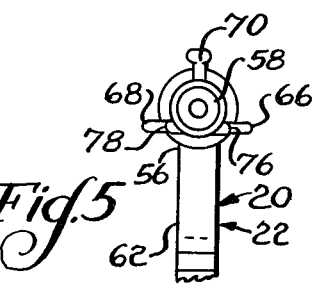
FIG. 5 is an end view of the sleeve assembly taken from the right hand portion of FIG. 2.

Referring now to FIGS. 1–9, there is shown a device generally designated 20 for performing an anesthesia procedure, and, in particular, a paracervical or transpudendal anesthesia procedure. The device 20 has a sleeve assembly 22, and a hollow needle assembly 24 slidably received within the sleeve assembly 22. With reference to FIGS. 8 and 9, the needle assembly 24 has an elongated hollow needle 26 defining a lumen 28 and having a distal tip 30. A proximal end 32 of the needle 26 is secured to a proximal connection member 34 having a proximal port 36 to receive the tip of a syringe. The connection member 34 has an elongated hollow tubular section 40 covering a proximal portion of the needle 26. The connection member 34 also has an elongated distally directed control member 38 which is generally aligned with and spaced from the needle 26 and the tubular section 40. As shown, the control member 38 has an inwardly directed hook 42 at a distal portion 44 of the control member 38, with the hook 42 being spaced from the tubular section 40 and needle 26.

With reference to FIGS. 2-7, the sleeve assembly 22 has an elongated hollow sleeve 46 defining a lumen 48 to receive the needle 26, with the sleeve assembly 22 having a hollow placement member 50 attached to a distal end 52 of the sleeve 46. As shown, a proximal end 54 of the sleeve 46 is attached to a distal portion of an abutment member 56, with the abutment member 56 having a proximal port 58, and a lumen 60 communicating between the port 58 and the lumen 48 of the sleeve 46. The abutment member 56 has a lower ring 62 to receive the user's thumb during use of the device. The abutment member 56 has a lower laterally extending plate 64 defining a pair of outwardly directed side flanges 66 and 68 extending longitudinally along the abutment member. The abutment member 56 also has an upwardly directed flange 70 extending longitudinally along the abutment member, and having a length approximately equal to the length of the flanges 66 and 68.

The abutment member 56 has an outwardly directed annular rim 72 at a proximal end of the abutment member. The abutment member has a laterally extending proximal first stop member 74 located on a proximal central portion of the plate 64, with the stop member 74 being spaced from the rim 72 a distance approximately equal to the length of the hook 42 of the needle assembly control member 38. Also, the flanges 66, 68, and 70 have proximal ends spaced a distance from the rim 72 a distance approximately equal to the length of the needle assembly hook 42. The abutment member 56 has a pair of spaced outwardly directed bosses 76 and 78 on a lower portion of the rim 72 for a purpose which will be described below. The abutment member 56 has a second intermediate stop member 80 extending laterally between the flanges 68 and 70. The abutment member 56 also has a third distal stop member 82 extending laterally between the flanges 66 and 70, with the third stop member 82 being located more distal than the second stop member 80, and with the first stop member 74 being located more proximal than the second stop member 80. The abutment member 56, sleeve 46, and placement member 50 of the sleeve assembly 22, as well as the connection member 34 of the needle assembly 24, may be made of a suitable plastic material, such that the control member 38 of the connection member 34 is slightly flexible.

With reference to FIGS. 8 and 10, in use a syringe S may be attached to a proximal end of the needle assembly 24 with the syringe tip T being received in the port 36 of the connection member 34. Next, with reference to FIGS. 3, 8, and 10, the needle 26 of the needle assembly 24 may be inserted through the lumens 60 and 48 of the sleeve assembly 22. As shown in FIGS. 10 and 11, the hook 42 of the control member 38 may be passed over the rim 72 on the abutment member 56 with the control member 38 flexing slightly during the transition past the rim 72. The needle assembly 24 is positioned at a first rotational position relative to the sleeve assembly 22 with the distal end 44 of the control member 38 engaging against the first stop member 74, and with the hook 42 received between the first stop member 74 and the rim 72 adjacent the outer surface of the abutment member. In this configuration, the first stop member 74 prevents distal movement of the needle assembly 24 while the needle tip is retracted within the sleeve assembly 22. Also, the hook 42 engages against the rim 72 of the abutment member 56, and prevents proximal movement of the needle assembly 22. In this configuration, the bosses 76 and 78 frictionally engage against the plate 64 to retard rotational movement of the plate 64 and needle assembly 24 in opposed angular directions to maintain the needle assembly 24 at the first rotational position, with the bosses 76 and 78 serving as guides to accomplish this result. In this configuration, the physician may insert his thumb through the ring 62 of the abutment member 56, and may grasp the distal end of the sleeve 46 with the first and second fingers, such that the device 20 may be inserted into the vagina with the needle 26 retracted within the sleeve assembly 22.

Next, the physician may select the distance the needle 26 projects from the sleeve assembly 22 by rotating the needle assembly 24 in different directions. In a first needle penetration orientation, the control member 38 is moved past the boss 78 while the hook 42 passes the flange 68 until the control member 38 is located intermediate the flanges 68 and 70 at a second rotational position. With reference to FIG. 12, the needle assembly 24 is then moved distally until the distal end 44 of the control member 38 engages against the second stop member 80, with the flanges 68 and 70 serving as guides to prevent rotational movement while the needle assembly 24 is located at the second rotational position with the second stop member 80 preventing distal movement of the needle assembly 24. In this configuration, the tip 30 of the needle 26 extends an intermediate distance, such as 0.25 inches, from the distal end of the sleeve assembly 22 to cause penetration by the needle 26 the intermediate distance into the patient's body. Once penetration of the needle 26 has been accomplished, the anesthetic solution may be pumped by the syringe S through the needle assembly 24 into the patient's body.

In an alternative orientation of needle penetration, the control member 38 may be moved from the first rotational position past the boss 76 while the hooke 42 passes the flange 66 until the control member 38 is located intermediate the flanges 66 and 70. With reference to FIG. 13, the needle assembly 24 may then be moved distally until the distal end 44 of the control member 38 engages against the third stop 82 which prevents further distal movement of the needle assembly 24 relative to the sleeve assembly 22. In this configuration, the needle assembly 24 is located at a third rotational position relative to the sleeve assembly 22, with the flanges 66 and 70 serving as guides to prevent rotational movement of the needle assembly 24 relative to the sleeve assembly 22. Also, in this configuration, the tip 30 of the needle 26 extends a maximum distance, such as 0.50 inches, from the distal end of the sleeve assembly 22 to cause maximum penetration by the needle. Once the needle tip 30 has penetrated the patient's body, the syringe S may be utilized to pump the anesthetic solution through the needle assembly 24 into the patient's body. After the anesthetic solution has been injected into the body, the needle 26 may again be retracted within the sleeve assembly 22 by moving the needle assembly to a proximal location with the hook 42 engaged against the rim 72, after which the needle assembly 24 is again rotated to the first rotational position with the needle tip 30 retracted within the sleeve assembly 22, as previously described.

Thus, in accordance with the present invention, the anesthesia device may be positioned within the patient's body while the needle tip is retracted within the sleeve assembly. The user may select penetration distances of the needle tip by rotating the needle assembly relative to the sleeve assembly in opposite directions, and by moving the needle assembly distally until it engages an appropriate stop member to cause penetration by the needle tip in a simplified manner.

The foregoing detailed description is given for clearness of understanding only, and no unnecessary limitations should be understood therefrom, as modifications will be obvious to those skilled in the art.

I claim:

1. A device for performing an anesthesia procedure on a patient, comprising:

a needle assembly having an elongated hollow needle with a distal tip, and a connecting member attached to a proximal end of the needle, with said connecting member having a elongated distally directed control member generally aligned with and spaced from the needle; and a sleeve assembly having an elongated hollow sleeve to slidably receive the needle, and an abutment member attached to a proximal end of the sleeve, said abutment member having a first proximal stop member to abut against a distal portion of the control member in a configuration of the needle assembly at a first rotational position with the needle tip retracted within the sleeve assembly, and guide means to releasably retain the needle assembly at the first rotational position, said abutment member having a second intermediate stop member to abut against the distal portion of the control member in a configuration of the needle assembly at a second rotational position with the needle tip extending an intermediate distance from the sleeve assembly, and guide means to releasably retain the needle assembly at the second rotational position, and said abutment member having a third distal stop member to abut against the distal portion of the control member in a configuration of the needle assembly at a third rotational position with the needle tip extending a maximum distance from the sleeve assembly, and guide means to releasably retain the needle assembly at the third rotational position.

2. The device of claim 1 wherein the first stop member is located between the angular positions of the second and third stop members.

3. The device of claim 1 wherein the control member has a distal inwardly directed hook located adjacent the outer surface of the abutment member.

4. The device of claim 3 wherein the abutment member has an outwardly directed annular rim adjacent a proximal end of the sleeve assembly, with said hook abutting against the rim to stop proximal movement of the needle assembly relative to the sleeve assembly.

5. The device of claim 4 wherein the distance between the first stop member and the rim is approximately equal to the length of said hook.

6. The device of claim 1 wherein the guide means associated with the first stop member comprises a pair of spaced outwardly directed bosses located on the abutment member proximal the first stop member, said bosses frictionally engaging against the control member to retard movement of the needle assembly in opposed angular directions.

7. The device of claim 1 wherein the guide means associated with the second stop member comprises a pair of spaced outwardly directed flanges extending on the abutment member proximally from opposed sides of the second stop member, said flanges receiving a distal portion of the control member and preventing rotational movement of the needle assembly when the control member is located intermediate the flanges, and said flanges being spaced from the proximal end of the abutment member to permit rotational movement of the needle assembly when the distal portion of the control member is located proximal the flanges.

8. The device of claim 1 wherein the guide means associated with the third stop member comprises a pair of spaced outwardly directed flanges extending on the abutment member proximally from opposed sides of the third stop member, said flanges receiving a distal portion of the control member and preventing rotational movement of the needle assembly when the control member is located intermediate the flanges, and said flanges being spaced from a proximal end of the abutment member to permit rotational movement of the needle assembly when the distal portion of the control member is located proximal the flanges.

* * * * *